United States Patent [19]

Battistel et al.

[11] Patent Number: 5,296,358
[45] Date of Patent: Mar. 22, 1994

[54] PROCESS FOR THE ENZYMATIC PREPARATION OF CEPHALOSPORANIC DERIVATIVES USING A D-AMINO ACID OXIDASE FROM *RHODOTORULA GLUTINIS* NCIMB 40412

[75] Inventors: Ezio A. Battistel, La Spezia; Pietro Cesti, Novara; Giuliana Franzosi, Milan; Vilhelmus van der Goes, Turin; Silvana Bonicelli, Bergamo; Mirella Pilone, Milan, all of Italy

[73] Assignee: Ministero Dell'Universita' e Della Ricerca Scientifica e Tecnologica, Rome, Italy

[21] Appl. No.: 893,048

[22] Filed: Jun. 3, 1992

[30] Foreign Application Priority Data

Jun. 3, 1991 [IT] Italy .................. MI 91 A 001509

[51] Int. Cl.$^5$ .................. C12P 35/06; C12N 9/02; C12N 9/04; C12N 9/06
[52] U.S. Cl. .................. 435/49; 435/47; 435/50; 435/51; 435/171; 435/189; 435/190; 435/191; 435/192; 435/255.1; 435/174; 435/911
[58] Field of Search .................. 435/47, 49, 50, 51, 435/171, 255.1, 189, 190, 191, 192, 174, 911

[56] References Cited

U.S. PATENT DOCUMENTS 3,436,310 4/1969 Arnold et al. .................. 435/47
3,658,649 4/1972 Arnold et al. .................. 435/47
3,912,589 10/1975 Smith et al. .................. 435/47

*Primary Examiner*—David M. Naff
*Assistant Examiner*—L. Blaine Lankford
*Attorney, Agent, or Firm*—Oblon, Spivak, McClelland, Maier & Neustadt

[57] ABSTRACT

The enzymatic preparation of cephalosporanic derivatives, or their salts, having the formula:

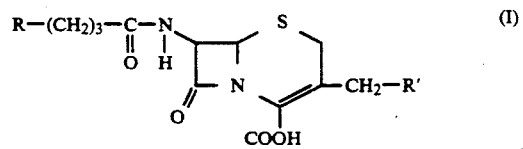

(I)

wherein R is —CO—COOH or —COOH, $R_1$ is H, OH, or —O—CO—R'' and R'' is an alkyl group with 1 to 4 carbon atoms, is carried out by the oxidative deamination of compounds, or their salts, having the formula:

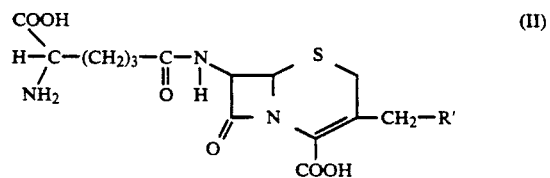

(II)

with an oxidase D-Aminoacid enzyme derived from *Rhodotorula glutinis* NCIMB 40412. The enzyme can be in a free or immobilized form.

13 Claims, No Drawings

PROCESS FOR THE ENZYMATIC PREPARATION OF CEPHALOSPORANIC DERIVATIVES USING A D-AMINO ACID OXIDASE FROM *RHODOTORULA GLUTINIS* NCIMB 40412

The present invention describes a process for the enzymatic preparation of cephalosporanic derivatives corresponding to formula I

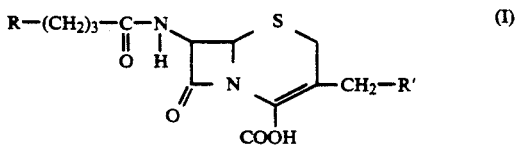

or their salts, wherein R represents a —CO—COOH or —COOH group and R' an H, OH, —O—CO—R" group, where R" represents a $C_1$-$C_4$ alkyl group.

More specifically, the invention relates to an enzymatic process for the conversion of derivatives of the cephalosporine C corresponding to formula (II):

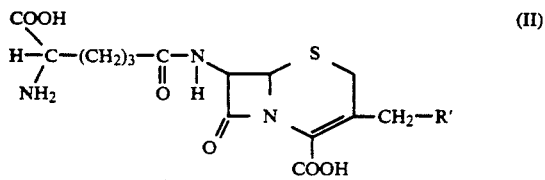

wherein R' has the above definition, in compounds corresponding to formula I, using a micro-organism, or enzyme therein contained, either free or immobilized, which is capable of selectively oxidizing the aminic group of the aminoadipic chain of compounds corresponding to formula II.

Cephalosporine C 3-acetoxymethyl-7- (D-5-amino-5-carboxypentamide) ceph-3-4-carboxylic acid can be converted into 3-acetoxymethyl-7-aminoceph-3-em-4-carboxylic acid (7-ACA) by removing the lateral aminoadipic chain of the β-lactamic ring. 7-ACA is a compound of great industrial interest, in that it is used in the synthesis of cephalosporanic derivatives having an antibacterial biological activity.

The deacylation of cephalosporine C, i.e. the elimination of the lateral D-5-amino-5-carboxypentanoyl chain, can be carried out chemically, for example using nitrosil chloride in formic acid in the presence of acetonitrile (U.S. Pat. No. 3,367,933). Another method of deacylation involves the protection of the carboxyl group of the aminopentenoic chain, reaction with phosphorous pentachloride at −55° C. and subsequent hydrolysis at low temperature with a mixture of water and methanol (Belgian Patent 718.824).

These methods must generally be carried out at low temperatures and require the use of costly and toxic solvents or reagents, which can cause serious problems of pollution and environmental impact. In addition, owing to the chemical instability of the β-lactamic ring and reactivity of the groups present in positions 3- and 7- of the ring, special reaction conditions must be applied (low temperatures, use of co-solvents) which make the process complex on an industrial scale.

Enzymatic methods are also known for removing the lateral aminoadipic chain in position 7 of the β-lactamic ring of cephalosporine C. For example it is possible to use specific acylases (French Patent 2,241,557, U.S. Pat. No. 4,774,179, European Patent 283.218) for selectively removing the D-aminoadipic chain of cephalosporine C. These processes, however, are often not reproducible and are characterized by low yields and lengthy reaction times.

On the other hand, processes which transform the cephalosporine C into 7-ACA by means of two enzymatic states are important from the industrial point of view. The first stage consists of using a D-aminoacid oxidase, such as one coming from a micro-organism of the Trigonopsis type (English Patent 1.272.769), which oxidizes the lateral D-5-amino-carboxypentanoyl chain in compounds corresponding to formula I. In the second stage, an acylase is used, for example that of a Pseudomonas-type micro-organism (U.S. Pat. No. 3,960,662), which deacylates the compounds having formula I in the corresponding derivatives of 7-ACA These enzymatic processes are interesting from an industrial point of view in that they make it possible to eliminate the problems related to the chemical synthesis with respect to the use and disposal of toxic compounds which are harmful to the environment.

The reactions are, in fact, carried out in a water environment, under moderate conditions of pH and temperature and do not involve the use of toxic substances or solvents.

The enzymes used in the first stage of these processes (D-aminoacid oxidase) are however characterized by a catalytic activity which is not very stable under operating conditions and by a sensitive lability of the bond between the prostetic part (cofactor) and the proteic part of the enzymatic molecule, Kubicek-Pranz, E. M. et al. (1985) J. Appl. Bioch. 7.104; Szwajcer-Dey, E. et al. (1990) Biochemistry International 20.1169.

It has now been found that it is possible to prepare compounds having formula I in a simple way, effectively and economically by means of a microbiological process which consists of the oxidative deamination of compounds corresponding to formula II using a micro-organism belonging to the Rhodotorula group or the D-aminoacid oxidase enzyme derived from it in a free or immobilized form. Particular advantages can be obtained by using as the enzymatic reagent the micro-organism classified as *Rhodotorula clutinis*, deposited at NCIMB (National Collections of Industrial & Marine Bacteria Ltd.) with number 40412 on 18/4/1991, which forms an integrant part of the present invention, as such or in the form of biologically pure cultures, or using one of its mutants or genetic material derived from it.

The present invention consequently relates to a process for the preparation of compounds corresponding to formula I which consists of reacting compounds having formula II in an aqueous buffer solution, with the enzyme D-aminoacid oxidase produced from *Rhodotorula glutinis*, from one of its mutants or from genetic material coming from *Rhodotorula glutinis* which is capable of selectively oxidizing the D-amino acid of the lateral chain of the cephalosporine C in position 7- into the corresponding acid or keto acid.

The process of the present invention is particularly effective in the preparation of the following derivatives included in formula I: 3-acetoxymethyl-7-β-(5-carboxy-5-oxopentanamide)-ceph-3-em-4-carboxylic acid and 3-acetoxymethyl-7-β-(4-carboxybutanamide)-ceph-3-em-4-carboxylic acid (glutaryl 7-ACA).

The micro-organism, also subject of the present invention, has the following characteristics:

Morphological characteristics: on agarized colture medium the colonies are pink/red in colour, have a mucoid consistency, shiny on the surface, with regular contours. The vegetative reproduction occurs by budding; the microscope does not reveal the presence of filaments. There is no sexual reproduction.

The micro-organism grows in 24-36 hours on YMG colture having the following composition:

| | |
|---|---|
| Yeast extract | 4 g/l |
| Malt extract | 8 g/l |
| Peptone | 5 g/l |
| Agar | 20 g/l |
| Glucose | 10 g/l |
| Growth temperature | 28-30° C. |

Biochemical characteristics: biochemical growth tests were carried out on different organic substrates, which are shown below together with the results obtained:

| | | | |
|---|---|---|---|
| Sorbitol | + | Galactose | + |
| D-Xylose | + | Actidione* | − |
| Ribose | + | Sucrose | + |
| Glycerol | + | N-acetyl-Glucosamine | − |
| Rhamnose | − | DL-lactate | − |
| Palatinose | + | L-Arabinose | + |
| Erythritol | − | Celbiose | + |
| Melbiose | − | Raffinoise | + |
| Glucuronate | − | Maltose | + |
| Melezitose | + | Trealose | + |
| Gluconate | − | 2-Keto-Gluconate | − |
| Levulinate | − | -Methylm-D-Glucoside | − |
| Glucose | + | Mannitol | + |
| Sorbose | − | Lactose | − |
| Glucosamine | − | Inositol | − |
| Esculine | − | | |

*Actidione = Cycloheximide

On the basis of the physiological data the micro-organism should be considered a *Rhodotorula glutinis*, in accordance with the classification and characterization of this yeast given by Barnett et al. in "Yeasts: Characteristics and Identification", Cambridge University Press, 1990.

The micro-organism used in the process of the present invention may be grown on a standard culture medium, using for example glucose as a carbon source, peptone and yeast extract as a nitrogen and vitamin source, at a pH of 5 to 6. Under these conditions, the *R. glutinis* produces the D-aminoacid oxidase enzyme even though in low quantities. It has been found however that it is possible to increase the expression level of the enzyme by the micro-organism, by adding inducers to the culture medium. For this purpose, D-aminoacids may be used as a sole nitrogen source, such as D-alanine or D-methionine, or, as an alternative, their racemic mixtures. These compounds may be added to the culture medium in concentrations ranging from 0.1 to 1.5%, preferably from 0.4 to 1% (w/v). As a carbon source glucose may be used in a concentration of 0.1 to 2%, preferably 0.8 to 1.5% (w/v).

The oxidation reaction cannot be carried out with the whole cells, and consequently the D-aminoacid oxidase enzyme contained in the *R. glutinis* must be extracted or released from the cells before being used. For this purpose, the cellular wall and/or membrane can be suitably permeabilized, for example using a solution of toluene and ethanol (2.5% v/v) at low temperature. Alternatively, it is preferable to use lysates or cellular extracts or enzymatic products with varying degrees of purification. For example, the cellular lysates may be prepared by suspending the cells in an aqueous buffer solution and breaking them both by means of vigorous stirring in the presence of glass pellets and by sonication via ultrasounds. The sample may be subsequently centrifugated to remove cellular deposits, whereas the D-aminoacid oxidase activity remains in solution in the supranatant. A further concentration and purification of the cellular extract may be obtained for example by means of fractionation by precipitation with ammonium sulphate or by treatment with polyfunctional resins such as Whatman CDR. A higher degree of purification may be obtained by weak ion-exchange resin column chromatography, hydrophobic interaction chromatoqraphy and by filtrating on gel.

The D-aminoacid oxidase enzymatic activity can be conveniently evaluated by measuring the consumption rate of the oxygen dissolved in water. This test can be carried out by polarography using a specific electrode for the oxygen [Pilone-Simonetta, M. et al. (1987) Biochim. Piophys. Acta 914, 136-142]. A D-aminoacid, or its racemic mixture, such as alanine is added to the enzyme sample at a steady temperature of 37° C. More specifically, the reaction is carried out in a 100 mM pyrophosphate buffer, pH 8.5, and 0.5% D-alanine as substrate, at 37° C.

The enzymatic activity (units per milliliter, U/ml, where a unit is the quantity of enzyme which transforms 1 μmole of substrate per minute) was defined as follows:

$$U/ml = v \times a \times (Vt/Vc)$$

wherein v is the initial consumption rate of the oxygen (in minutes), a is the solubility of the oxygen in water, Vt the total volume of the test mixture and Vc the sample volume.

Alternatively, the D-aminoacid oxidase enzymatic activity can be tested by measuring the formation rate of hydrogen peroxide by spectrophotometry. In fact, the oxidative deamination reaction takes place with an accompanying formation of hydrogen peroxide which can be titrated by reaction with 4-aminophenazone in the presence of dichlorophenylsulphonate and peroxidase (P. Trinder et al. (1984) Ann. Clin. Biochem. 21, 430-433).

The hydrogen peroxide which is formed during the reaction reacts with the peroxidase with the subsequent formation of a red-coloured quinonimine. More specifically, the reagent is prepared by dissolving dichlorophenylsulphonate 1 g/l, 4-aminophenazone 0.4 g/l and peroxidase 40 mg/l in a 100 mM pyrophosphate buffer, pH 8.5. D-alanine is added to the reagent as a substrate and also in the enzymatic sample. The units per milliliter, U/ml, are defined as follows:

$$U/ml = (DO \times Vt)/(19 \times Vc)$$

wherein DO is the optical density at 510 nm per minute, Vt is the total volume of the test mixturc, 19 the extinction coefficient of the quinonimine and Vc the volume of the enzymatic sample.

The oxidation reaction of the substrate corresponding to formula II is carried out in an aqueous buffer solution at a pH of 5 to 10, preferably 7 to 9, and at a temperature of 5° to 50° C., preferably 20° to 40° C. The substrate corresponding to formula II can be used up to a concentration of 20% (w/v), preferably 1 to 10%. The ratio substrate/enzyme may vary from 1 to 40 mg/unit of enzyme, preferably from 10 to 30. During the reaction air or oxygen is bubbled into the reaction mixture.

By treating compounds having formula II with D-aminoacid oxidase in the presence of the catalase enzyme, compounds corresponding to formula I are obtained, wherein R is the —CO—COOH group. This enzyme has the function of preventing the decarboxylation of the ketoacid owing to the hydrogen peroxide produced by the enzymatic deamination reaction, and consequently prevents the formation of the corresponding carboxylic acid. The catalase is normally present in the enzymatic complement of the R. glutinis, or in its cellular raw lysates.

To obtain a high yield in ketoacid, it may be necessary however to add the catalase to the reaction mixture. The amount of catalase to be added can vary from 0.01 to 0.5% (w/v). The catalase activity may be measured by means of spectrophotometry in accordance with the method of Aebi, H. (1974) in "Methods in enzymatic analysis", vol.2, 673–684, Bergmeyer, H. U., ed., Academic Press, N.Y. More specifically, hydrogen peroxide (concentration 30 mM) is added to the enzymatic test sample and the disappearance of the absorbance, due to the presence of the peroxide, is observed, at 240 nm as a function of time, at 25° C.

Compounds having formula I wherein R is the —COOH group are produced by treating compounds having formula II with D-aminoacid oxidase as described above, without catalase activity, using sufficiently purified enzymatic preparations and carrying out the reaction in the presence of catalysis inhibitors. Suitable inhibitors may be ascorbic acid or sodium azide, which are generally used in concentrations of 1 to 100 mM.

The complete oxidation process is carried out by vigorously stirring the mixture composed of the substrate corresponding to formula II, of the biocatalyst, of the catalase (when ketoacids having formula I wherein R is the —CO—COOH group, are to be produced) in an aqueous buffer solution, by bubbling in air or oxygen.

The aeration of the mixture is important for obtaining and effective conversion. Generally aeration by bubbling 1 volume of gas/system volume/minute is sufficient for a good yield.

The D-aminoacid oxidase may be used either free or immobilized. The enzyme can be appropriately immobilized on either synthetic or natural polymer supports suitably funtionalized to allow the covalent linkage of the proteic molecule. For example, agarose (Pharmacia) may be used, or aminoalkylated glass with controlled porosity (CPC, 500 A, Pierce), aminoalkylated silica (Fluka, 375 A), Duolite (polystyrene polymer, Rohm and Haas).

At the end of the reaction, the compound having formula I can be extracted from the solution, after acidification, with a suitable organic solvent such as n-butanol or ethyl acetate. Alternatively, the reaction product may be more conveniently extracted using anionic exchange resins, such as Amberlite IRA 400 I, or absorbent resins, such as Amberlite XAD-2. The product can be recovered by washing the resin with a saline solution (for example carbonate) or with a suitable organic solvent (for example acetone or methanol). Alternatively, the reaction mixture may be directly used in the deacylation reaction for the production of 7-ACA.

EXAMPLE 1

Cultures in liquid were prepared in 500 ml flasks containing 100 ml of organic medium in the presence of 0.2% of yeast extract, 0.5% of malt extract, 0.9% of D-alanine, pH 6. After 30 hours of fermentation (optical density at 660 nm of about 5), the cells where centrifuged and resuspended in a 100 mM phosphate buffer, pH 7.5, 5mM mercaptoethanol, 2 mM EDTA, and collected for centrifugation after two washings. A cellular extract was prepared by subjecting the cells, suspended in the previous buffer with the addition of 0.3% cetylpyridine bromide, to mechanical breakage using glass beads (0.5 mm in diameter) under vigorous stirring, in the following proportion: 1 gram of cells/10 grams of beads/7ml of buffer. Five breaking cycles (60") were carried out. The homogenate was filtered on a buckner adding a few drops of 2-octanol to reduce the formation of foam and was then centrifugated for 1 hour at 18,000 rpm. The supranatant was used for the reaction with the cephalosporin C. 70 ml of 100 mM pyrophosphate buffer, pH 8, 100 mg of catalysis (Sigma, 2900 U/mg and 1 g of cephalosporin C were added to 30 ml of supranatant (15 U/ml, specific activity 0.6 U/mg protein (the concentration of protein was estimated by means of the Bradford method, M. H., 1976, Anal. Biochem. 72,248–254). The reaction temperature was regulated at 37° C., and air was bubbled into the mixture. The almost total disappearance of the substrate was observed in about 60 minutes and also the formation of the deamination product, 3-acetoxymethyl-7-$\beta$-(5-carboxy-5-oxopentanamide)-ceph-3-em-4-carboxylic acid. The conversion into ketoacid was 93%, controlled by HPLC (RP C18 Merck column 15×0.46 cm, 25 mM phosphate buffer eluant, pH 4.5 and acetonitrile, 91:9, flow rate 0.6 ml/min).

The solution was cooled to 0° C., saturated with ammonium sulphate, centrifugated, acidified to pH 3 with hydrochloric acid and extracted with ethyl acetate (100 ml for 4 times).

The orqanic phase, washed with a saturated solution of ammonium sulphate, was made anhydrous with sodium sulphate and concentrated. The product was then crystallized by ethyl acetate/hexane. 400 mg of ketoacid were obtained (elemental analysis: C 16H 18N 20 9S, calculated C, 46.35; H, 4.4; N, 6.76; S,7.75%, actually found C,46.12; H,4.2; N,6.85; S,7.7%).

EXAMPLE 2

The reaction was carried out under the same conditions as described in Example 1, without the addition of catalase, but in the presence of one of its inhibitors, sodium azide in a concentration of 50 mM. The reaction mixture was kept under aeration by bubbling in air and at a thermostatic temperature of 37° C. In about 60 minutes the cephalosporin C had almost completely reacted and the reaction product had formed, i.e. 3-acetoxy-methyl-7-$\beta$-(4-carboxybutanamide)-ceph--3-em-4-carboxylic acid (glutaryl-7-ACA). The conversion into glutaryl-7-ACA was 91%, measured by means of HPLC, as described above.

The reaction mixture was treated with the absorbent resin Amberlite XAD-2 (20 g). The resin was subsequently filtered, washed with water and then with methanol (200 ml). The organic phase was concentrated under vacuum and the product crystallized from ethyl acetate/hexane. 440 mg of glutaryl 7-ACA were obtained (elemental analysis: c 15H 18N 20 8S, calculated:

C,46.63; H,4.70; N,7.25; S,8.30%, actually found: C,46.41; H,4.62; N,7.45; S,8.38%).

EXAMPLE 3

Ammonium sulphate up to a 30% saturation at 4° C. was added to the cellular lysate (200 ml) prepared as described in Example 1, 2 U/ml, 0.3 U/mg protein. The solution was left to decant for 1 hour and was then centrifuged at 10,000 rpm for 30 minutes. Ammonium sulphate up to a 60% saturation was added to the supranatant. The suspension was left to decant for 1 hour and was then centrifuged at 15,000 rpm for 30 minutes. The sediment, resuspended in 5 ml of 10 mM potassium pyrophosphate buffer, pH 7.5, EDTA 2mM, glycerol 15% and 5 mM mercaptoethanol, was dialyzed against the same buffer. 7 ml of enzymatic solution (50 U/ml, 0.4 U/mg) were thus obtained. The enzyme was further purified by DEAE-Sephacel column chromatography equilibrated with the same buffer. The fractions not withheld and eluated from the column were concentrated to obtain 10 ml of enzymatic solution, 20 U/ml, 12 U/mg. The D-aminoacid oxidase partially purified as described above, was used for the reaction with the cephalosporin C. 7.5 ml of 100 mM pyrophosphate buffer, pH 8 and 100 mg of cephalosporin C were added to 2.5 ml of this solution. The temperature of the mixture was regulated at 37° C. for about 90 minutes, and air was bubbled in. In this way, the almost total conversion of the cephalosporin C into 3-acetoxymethyl-7-β-(4-carboxybutanamide)-ceph-3-em-4-carboxylic acid (glutaryl-7-ACA) was obtained. The conversion was equal to 91% in glutaryl-7-ACA, measured in HPLC under the conditions previously described.

What is claimed is:

1. A process for the enzymatic preparation of a cephalosporanic derivative, or a salt thereof, having the formula (I)

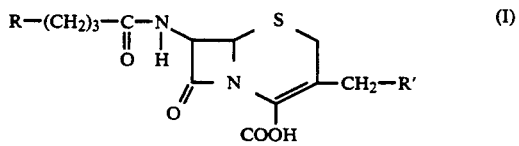

wherein R is a —CO—COOH or —COOH group, and R' is H, OH, or —OCO—R", and R" is an alkyl group with from 1 to 4 carbon atoms, said process comprising oxidatively deaminating a compound, or a salt thereof, having the formula (II)

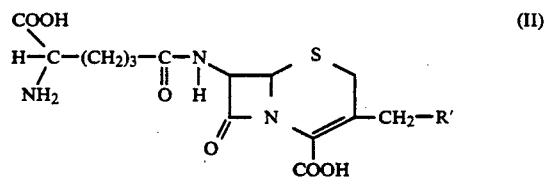

in the presence of the D-amino acid oxidase enzyme extracted from the microorganism *Phodotorula glutinis* NCIMB 40412 or a mutant thereof capable of producing said enzyme.

2. The process of claim 1, wherein said deaminating is carried out in a buffer soluton at pH 5 to 10.

3. The process of claim 1, wherein said deaminating is carried out at a temperature of from 5 to 50° C.

4. The process of claim 1, wherein said deaminating is carried out with a starting concentration of said derivative, or salt thereof, having formula (II) of 1 to 10% w/v.

5. The process of claim 1, wherein said deaminating is carried out such that the ratio of said derivative, or salt thereof, of formula (II) to said enzyme is 1 to 40 mg/unit of enzyme.

6. The process of claim 1, wherein said deaminating is carried out in the presence of 0.01 to 0.5% (w/v) of a catalase enzyme.

7. The process of claim 1, wherein said deaminating is carried out in the presence of an inhibitor of catalase.

8. The process of claim 7, wherein said inhibitor of catalase is selected from the group consisting of ascorbic acid and sodium azide and said inhibitor of catalase is present in a concentration of 1 to 100 nM.

9. The process of claim 1, wherein the reaction is carried out in an aqueous buffer solution.

10. The process of claim 1, wherein the reaction is carried out in a buffer solution at a pH range from 7 to 9.

11. The process of claim 1, wherein the reaction is carried out at a temperature ranging from 20° to 40° C.

12. The process of claim 1 wherein the reaction is carried out at a concentration of the substrate having formula II of up to 20% w/v.

13. The process of claim 1 wherein the reaction is carried out at a ratio substrate/enzyme of from 10 to 30 mg/unit of enzyme.

* * * * *